United States Patent [19]
Ahlert

[11] Patent Number: 4,605,172
[45] Date of Patent: Aug. 12, 1986

[54] SENSORY APPARATUS

[75] Inventor: Dieter Ahlert, Ostercappeln, Fed. Rep. of Germany

[73] Assignee: Dierks & Söhne GmbH & Co. KG, Osnabrueck, Fed. Rep. of Germany

[21] Appl. No.: 656,629

[22] Filed: Oct. 1, 1984

[30] Foreign Application Priority Data

Oct. 5, 1983 [DE] Fed. Rep. of Germany ....... 3336218

[51] Int. Cl.⁴ .............................................. B02C 25/00
[52] U.S. Cl. ......................................... 241/33; 73/54; 366/142
[58] Field of Search ........................... 366/142; 73/54; 241/33–36, 101 B, 30

[56] References Cited

U.S. PATENT DOCUMENTS 3,382,706 5/1968 Fitzgerald et al. ................. 73/54 X
4,511,093 4/1985 Ohkoshi et al. ............ 241/101 B X

FOREIGN PATENT DOCUMENTS 2653864 10/1981 Fed. Rep. of Germany.
2257083 8/1975 France .................................... 73/54
1564201 4/1980 United Kingdom.
393643 12/1973 U.S.S.R. ................................. 73/54

Primary Examiner—Mark Rosenbaum
Attorney, Agent, or Firm—Jordan and Hamburg

[57] ABSTRACT

A sensory apparatus for substances containing granular particles which are to be moved or mixed in a casing includes a sensor which is supported on a wall of the casing and protrudes from the wall into the area of the moving substances. The sensor has a deflectable plate by which the sensor is connected to the surface of the wall and has on its outer side at least one measurement receiver providing signals indicating the mixing conditions.

15 Claims, 3 Drawing Figures

SENSORY APPARATUS

BACKGROUND OF THE INVENTION

This invention relates to a sensory apparatus of the type as already known from Federal Republic of Germany Patent DE-PS No. 26 53 864. Such sensory apparatus, based upon its response sensitivity and its broadband signal detection and signal transmission, can distinguish the state of the substances passing by the apparatus, particularly substances to be mixed or granulated in the container. The apparatus can distinguish the state of the substances as regards the particle size and frequency as well as the viscosity of the contents of the container, whereby the apparatus indicates not only an average value of the "kinetic energy" exerted on the sensor by the substance passing by the sensor, but also, in a given case, a spectrum of impulse signals according to the occurrence of particles.

The previously-known designs are longitudinally stretched whereby the sensor is positioned on the head of a bending rod and extensometer strips are provided on a bending zone adjacent to a fixed clamping area on the foot side of the sensor for converting the mechanical bending stress into electrical signals. The sensory apparatus is designed like a telescope rod, whereby the sensor, and the foot of the sensor, with the measuring elements positioned thereon, is enclosed by a tube portion which is positioned inside of a further sleeve which is connected on its side to the wall of the container. This construction of the sensory apparatus takes into consideration the practical requirement, which is not stated in the aforementioned patent, that the sensor can be retracted into the sleeve when no measuring results are required. This prevents damaging of the exposed sensor, for instance, when chunky substances are put into the container for mixing. Accordingly, in the practically known sensory apparatus, the sensor is fastened on the cover of the container so that it can be retracted from the area where the substances are to be mixed.

Retracting the sensor, however, results only in a limited mechanical protection and, furthermore, the foot section of the sensor remains exposed to soiling as well as to chemical and thermal reactions. Furthermore, the telescoping feature of the sensor is constructionally expensive and inconvenient during measurements because, on the one hand, in order to provide a protected retracting position, the sensory apparatus has to be positioned in the cover of the container but, on the other hand, a sufficient sliding length has to be provided so that it can reach into the area where the substance is being moved in the container.

Accordingly, an object of the present invention is to create a sensory apparatus which significantly reduces the abovementioned disadvantages and which provides simple and fast measurements at high operational reliability.

The present invention deviates from the generally rodshaped construction of the aforementioned sensor. According to the present invention, the actual sensor head extends from the wall, whereas the deformation area which is provided for measurement detection is in the form of an extended area, preferably a membrane-like foot. The extended area can be arranged flat in the wall of the container. This flat configuration is especially important when the substances in the container are being moved by a throwing movement, for instance, as is the case of a configuration of a mixing implement which is near, or at, the ground, and which generates a funnel movement whereby the walls contribute to forming a funnel. A foot, adapted to the wall, makes possible an interference-free configuration of the funnel.

The reduced measurements and mass of the apparatus improve the response sensitivity of the sensor and the bandwidth of the signal, whereby the compact design simultaneously results in suppressing interfering self-oscillations.

Because of the configuration of the foot which lies flat on the wall and because of the total height of the sensory apparatus extending into the container, which is essentially reduced to the head of the sensor, the sensory apparatus is not much stressed. Also, because of its sturdier design, it can withstand even coarser materials in the container. The sensor no longer needs to be equipped with a retraction position. This allows constructing the sensory apparatus without "moving parts", that is, without telescoping sliding parts, as well as without the corresponding drives and controls. Thus the sensory apparatus is simple and sturdier and is constantly ready for operation.

The greater strength of the sensory apparatus also makes it possible to position it in a deeper lying wall area of the container, rather than in the cover as was previously done. This allows it to reach the substances to be mixed even if the container is only partially filled. Limited measuring conditions which so far had to be taken into consideration, such as requiring a given high degree of fullness of the container for creating sufficient impact of the substances on the sensor, are no longer applicable.

The deformable plate simultaneously forms a separation wall, on the one side between the sensor head and, on the other side, between the measuring receiver which protects the latter mechanically and chemically. Essentially, various mechanical and electrical signal converters can be utilized behind the deformable plate. Preferably, tested extensometer strip elements are used for this purpose. They are bonded to the backside of the deformable plate and signal the deformation of the plate.

The deformable plate can be configured in various shapes, such as, for instance, in band-like laterally extending shapes, for a sensor having from the outset a fixed triggering direction. Preferably, an extended elastic surface membrane is used as a deformable plate whereby the surface extension allows the positioning of distributed measuring receivers, and accordingly, also the analysis of the signals in regard to the triggering direction for the sensor.

Other features which are considered characteristic of the invention are set forth in the appended claims.

Although the invention is illustrated and described in relationship to specific embodiments, it is nevertheless not intended to be limited to the details shown, since various modifications and structural changes may be made therein without departing from the spirit of the invention and within the scope and range of equivalents of the claims.

The construction and operation of the invention, however, together with additional objects and advantages thereof will be best understood from the following description of specific embodiments when read in connection with the accompanying drawings.

DESCRIPTION OF THE PREFERRED EMBODIMENTS

Figure 1:
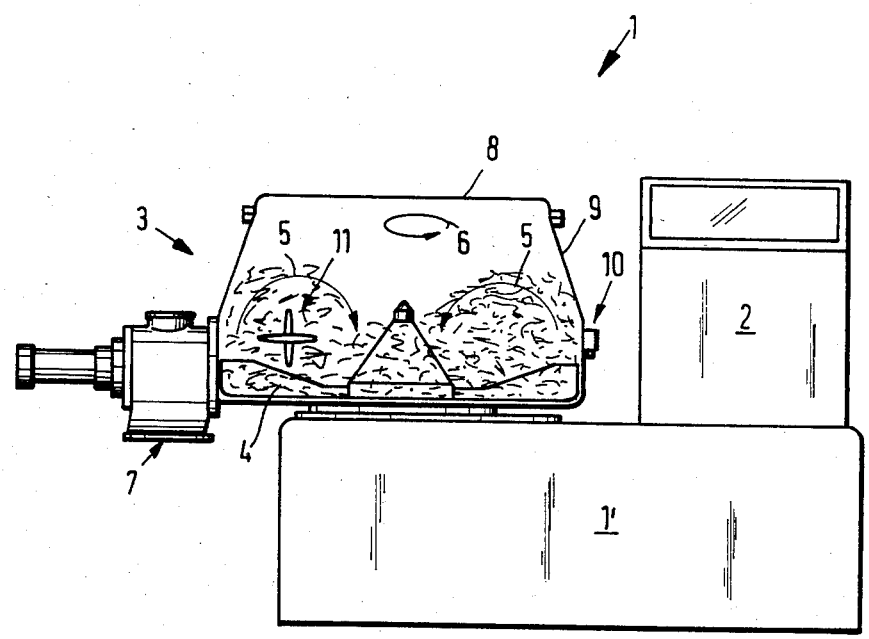
FIG. 1 is a schematic side view and partial cross-section of a mixing apparatus.

FIG. 1 shows a conventionally-known mixer represented as a unit by the numeral 1. The mixer is mounted on a housing 1' which includes a control console 2 and a container 3. A mixing implement 4 rotates in the container 3 at a relatively high speed so that the substances contained in the container 3 execute a funnel-like movement. This movement includes the peripheral rising of the substances, and the subsequent falling back into an inner area in the direction of the arrow 5, as well as the rotation together with the mixing implement 4 around the axis of the container in the direction of the arrow 6. At 7 is indicated a discharge device as is commonly used on such containers in addition to various devices for supplying and discharging materials, liquids, gases, or for applying heat, vacuum, pressure, etc.

The casing 9 of the container 3 which is cylindrical at the bottom and then conically narrowing into a container cover 8 contains a sensory apparatus which is indicated as a unit as 10 and which is described in greater detail hereinafter. The sensory apparatus 10 is disposed in the lower cylindrical portion of the container casing 9 closely above the path of motion of the mixing implement 4.

Viewed in the rotational direction of the mixing implement 4, the sensory apparatus 10 is positioned at an angle of approximately 140° in front of or in advance of a conventional type crushing device 11 which also is positioned in the lower area of the container casing 9 and which extends from the outside into the container. The installation of the sensory apparatus in front of the crushing device has proven to be advantageous because the crushing device influences the funnel-shaped movement of the substances to be mixed, whereby this influence at first steadily decreases along the circumference (in the rotational direction of the mixing implement and of the substances), and then increases again shortly before the crushing device, due to the localized retroaction. In order to eliminate this influence of the crushing device 11 which generally has to be considered a disturbance variable, the mixing implement 4 is positioned at an angle distance of approximately 140° in front of the device.

Figure 2:
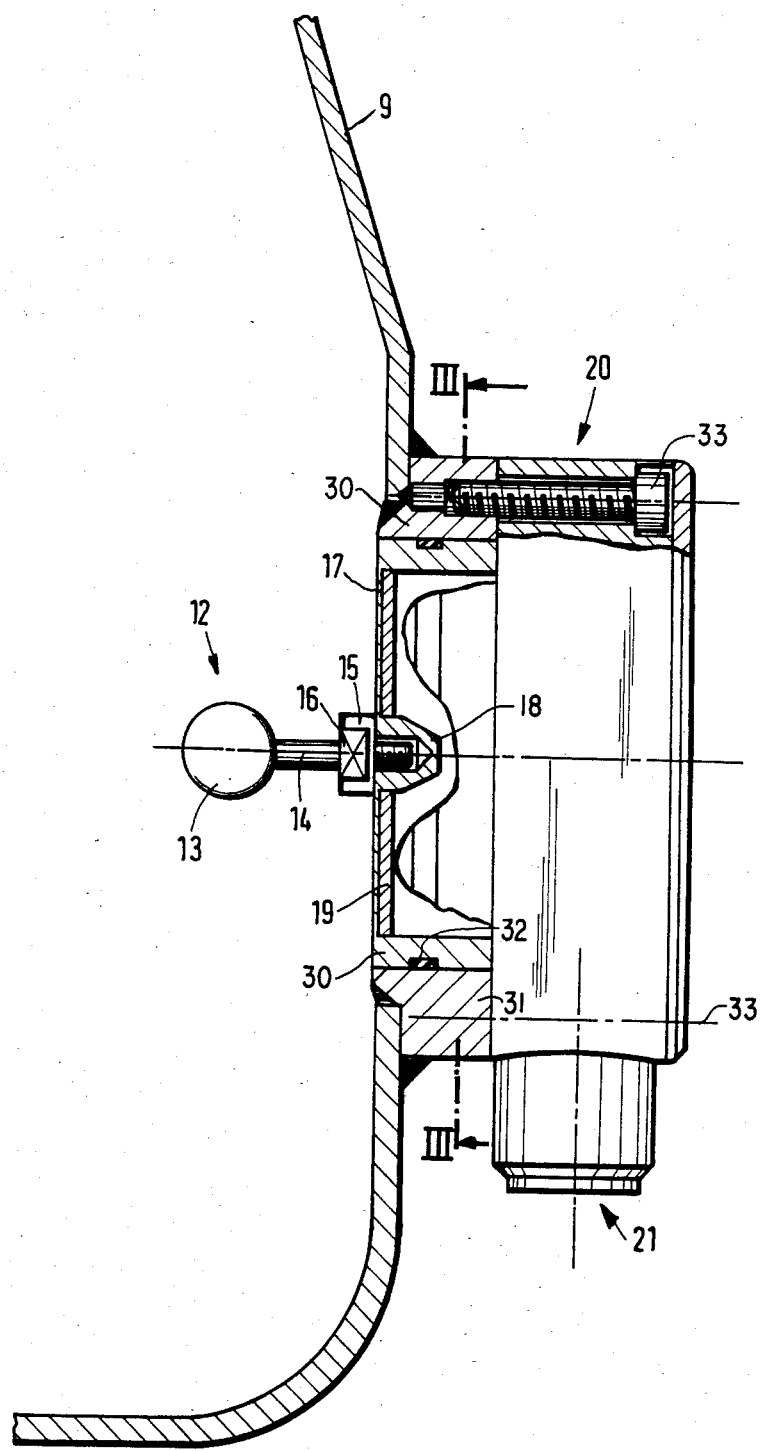
FIG. 2 is an enlarged partial detail view of FIG. 1 showing a section of the mixing container with a sensory apparatus.
Figure 3:
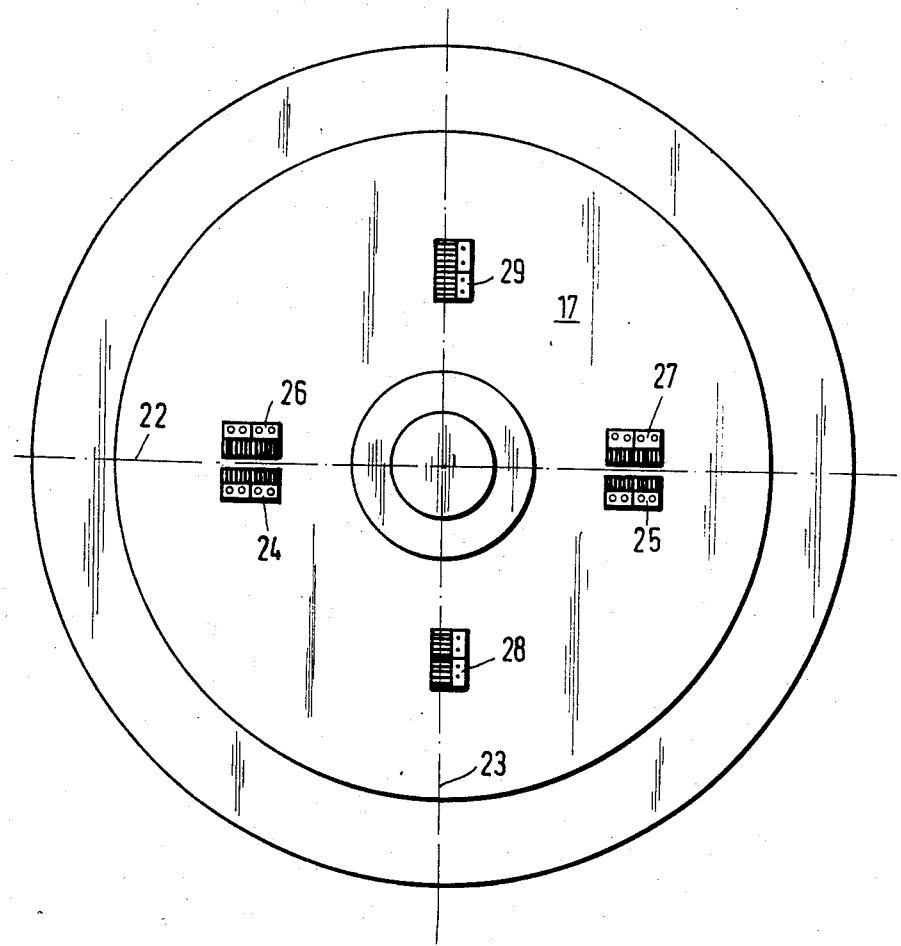
FIG. 3 is a cross-sectional view taken along the line III—III of FIG. 2.

FIG. 2 shows an enlarged representation of an area of the container wall 9 from which protrudes a short sensor 12 having a ball-shaped head 13 and cylindrical rod or collar 14 extending towards the inside of the container. In order to respond to the occurrence of fine particles, this configuration is of low mass, but it is also sufficiently strong to withstand the impact of more massive substances. In relation to the substances, the ball head shape is advantageous to the flow and, at the same time, is not very prone to soiling. In addition, the thinner rod or collar 14 suppresses the settling of soil particles in the direction of the wall. The sensor 12 is fastened on a screw base 15 of a flat face 16 in the center of a deformable metal plate or membrane 17, the plate 17 being of a circular form, as shown in FIG. 3. The plate 17 is positioned in the container wall and is provided in the center with a screw base 18 for the sensor 12. The screw base allows for exchanging the sensor and the selective utilization of sensors of various sizes and/or masses, but, alternatively, it can also be eliminated in favor of a fixed connection.

When a mixing movement is produced in the container 3, the movement causes pasty or granular substances in the container to impinge upon the sensor 12 and, according to the kind of stress produced, it is evenly, or also pulsatingly, deflected, whereby the deflection is transmitted to the plate 17 which causes it to deform.

On the backside of the plate 17, protected inside a layer of grouting 19, are positioned extensometer strips which measure the deformation of the plate 17 and which emit signals representing the deformation to an essentially known analyzing device which is not shown in the drawings. The analyzing device is positioned in a housing separated from the container 3. Only the actual sensory apparatus with a housing 20 ending into a cable bushing 21 is positioned on the container.

FIG. 3 shows a rear view of the deformable plate 17 and shows the positioning of the extensometer strips (however, without the corresponding wiring). The circular plate 17 is divided by two diametric lines 22 and 23 which are perpendicular to each other and along which are positioned the extensometer strips. The main direction is thereby determined by the diametric line 22 on which are positioned four extensometer strips 24, 25 and 26, 27. These four extensometer strip elements are disposed in opposite pairs on the same diameter, whereby the extensometer strips 24 and 26, as well as the extensometer strips 25 and 27, are positioned closely together so that they can be evaluated in pairs within a bridge circuit for temperature compensation.

When the sensor 12 is joltingly, or evenly, stressed along the diametric line 22, then the extensometer strip pairs pick up the various deformations and indicate the corresponding oppositely directed signal changes as a measurement of the stress, whereby the frequency characteristic of these extensometer strips transmits pulsating signals.

Along the diametric line 23 are positioned two diametrically opposite extensometer strips 28 and 29, which do not react when the sensor 12 picks up a stress in the direction of the diametric line 22, but only when at least one of the directional components of the stress falls on the diametric line 23. With this configuration, it is possible to suppress directional changes by combining the stress only of the correct components. It is also possible to determine the direction of the stress which gives additional information concerning the movement of the substances to be mixed in the container. It is also suitable and useful for the analysis.

The described sensory apparatus, despite all of its strength, provides sensitive and constant monitoring of the substances to be mixed in the container as long as the substances are being moved. This makes it possible to improve the already utilized monitoring of substances to be mixed, in particular in the pharmaceutical processing sector, by adding a high degree of exactitude and reproducibility, by simplifying it, and by extending monitoring to constant monitoring. The configuration of lying flat on the wall, in conjunction with the low total height and lower sensor mass, makes it possible to abandon altogether moving parts and their corresponding drives and controls. The positioning in the lower area of the container permits measurements even when the container is only partially filled as well as abandoning special service and test measures regarding the sealing of the container in the area of the sensory apparatus because movement gaps no longer exist there.

Also, the installation and the eventual changing of the sensory apparatus is simply executed, as can be seen from FIG. 2. The sensory apparatus is provided with a support 30 which protrudes in a position facing the housing 20. The support 30 is inserted from the outside into a fastening ring 31 fixed on the container and is additionally sealed by a ring packing 32. Tightening screws 33 secure the sensory apparatus into its installation position between the housing 20 and the tightening ring 31. The sensory apparatus, either for exchanging it or for a thorough cleaning, can be removed from its installation position at any time.

An example of the material out of which the deflectable plate 17 is made is stainless steel.

What I claim is:

1. Sensory apparatus for substances being mixed in a container comprising a container having a wall with an opening, a deflectable plate member disposed over said opening in said wall and which forms a continuation of said wall, a sensor element connected to said plate member and protruding from the inside of said plate member into the container and into the path of movement of the substances being mixed in the container such that said plate deflects depending on the mixing conditions in said container, and sensor detectors externally of said container on the outside of said plate member sensing the deflection of said plate member and providing signals indicative of said deflection and thereby indicative of the mixing conditions in said container.

2. Sensory apparatus according to claim 1, wherein said sensor detectors are extensometer strips substantially equidistantly spaced from said sensor element.

3. Sensory apparatus according to claim 1, wherein said deflectable plate member has a circular configuration, said sensor detectors being positioned along a diametric line substantially equidistant on opposite sides of said sensor element.

4. Sensory apparatus according to claim 1, wherein there are at least two sensor detectors positioned generally along a first diametric line of said deflectable plate member and at least two detectors positioned generally along a second diametric line of said deflectable plate member.

5. Sensory apparatus according to claim 4, wherein said first and second diametric lines are perpendicular to one another.

6. Apparatus comprising a container for substances being mixed, said container having a side wall, means on said side wall defining an opening, sensor means mounted within said opening, said sensor means comprising a deflectable plate member disposed over said opening in said wide wall and which is continuguous with said side wall to form a continuation of said side wall, said sensor means further comprising a sensor element connected to said plate member and protruding from the inside of said plate member into the container and into the path of movement of the substances being mixed in the container such that said plate deflects depending on the mixing conditions in said container, and sensor detectors externally of said container on the outside of said plate member sensing the deflection of said plate member and providing signals indicative of said deflection and thereby indicative of the mixing conditions in said container.

7. Apparatus according to claim 6, wherein said sensor means comprises sealing means for sealingly mounting said plate member in said opening such that the back of said plate member is sealed from the inside of said container, whereby said sensor detectors are not exposed to the substances being mixed.

8. Apparatus according to claim 7 further comprising a housing on the outside of said container, said housing being disposed over the outside of said plate member, and mounting means detachably mounting said housing on said container such that said housing can be detached from the housing to provide for access and replacement of said sensor means from the outside of said container.

9. Apparatus according to claim 6, wherein said container has a bottom wall extending from said side wall, said side wall having an upper edge, said opening being located below said upper edge.

10. Apparatus according to claim 9, wherein said side wall of said container and said plate member are generally vertically disposed.

11. Apparatus according to claim 6, further comprising a mixing implement in said container producing a funnel-shaped mixing movement in said container, said sensor element extending from said container side wall into the path of said funnel-shaped mixing movement.

12. Apparatus according to claim 6, further comprising a chopping device in said container extending from said container side wall into the container, said sensor element being positioned in a rotational direction ahead of the chopping implement.

13. Sensor apparatus according to claim 12, wherein said sensor element is positioned in the rotational direction about 140 degrees ahead of the chopping implement.

14. Apparatus according to claim 6, further comprising mounting means for detachably mounting said deflectable plate member in said opening in said container side wall.

15. Apparatus according to claim 14, wherein said mounting means comprises a ring fixedly mounted in said opening in said container side wall, a sleeve insertable in said ring and mounting said deflectable plate member, and threaded means threaded into said ring for mounting said sleeve on said ring.

* * * * *